United States Patent [19]
O'Hara et al.

[11] Patent Number: 4,476,342
[45] Date of Patent: Oct. 9, 1984

[54] PREPARATION OF HIGHLY BRANCHED CHAIN OLIGOMERS

[75] Inventors: Mark J. O'Hara; Tamotsu Imai, both of Mount Prospect, Ill.

[73] Assignee: UOP Inc., Des Plaines, Ill.

[21] Appl. No.: 510,480

[22] Filed: Jul. 1, 1983

[51] Int. Cl.$^3$ .............................................. C07C 2/24
[52] U.S. Cl. .................................................. 585/514
[58] Field of Search ........................................ 585/514

[56] References Cited

U.S. PATENT DOCUMENTS 2,060,871  11/1936  Ipatieff ................................ 585/514

FOREIGN PATENT DOCUMENTS

50/30046  9/1975  Japan .

Primary Examiner—Curtis R. Davis
Attorney, Agent, or Firm—James Hoatson, Jr.; Raymond H. Nelson; William H. Page, II

[57] ABSTRACT

Oligomers of olefins containing from 3 to about 6 carbon atoms such as dimers may be obtained in a more highly branched chain compound by effecting the oligomerization at temperatures in the range of from about 50° to about 350° C. and a pressure in the range of from about 100 to about 2500 psig in the presence of a catalyst comprising a fluorided aluminum phosphate. The catalyst may be prepared by impregnating an aluminum phosphate with a fluorine-containing compound in an aqeous or nonaqueous medium, drying, calcining and recovering the desired catalyst.

12 Claims, No Drawings

PREPARATION OF HIGHLY BRANCHED CHAIN OLIGOMERS

BACKGROUND OF THE INVENTION

In recent years, automotive engines which utilize gasoline as a fuel therefor have required, due to technological advances, gasolines which possess a relatively high octane rating. This high octane rating is necessary in order to prevent premature ignition of the fuel in the engine, thus resulting in what is commonly known as a "knock." One method of obtaining the necessary octane rating which will prevent this malfunction is to prepare a blend of additives in a gasoline obtained by conventional refining processes as opposed to more expensive refining operations which will produce a gasoline having a high octane rating per se. Among organic compounds which themselves possess high octane ratings and are therefore utilized as additives to boost the octane rating of relatively low grade gasolines are aromatics and highly branched olefins or paraffins. It is therefore necessary to provide a process for obtaining the latter compounds, that is, the highly branched olefins or paraffins which may be utilized as additives to improve the octane rating of gasolines or, if so desired, may be utilized themselves as a high octane gasoline.

As will hereinafter be shown in greater detail, it has now been discovered that highly branched chain compounds may be obtained from normal olefins utilizing a particular type of acidic catalyst.

BRIEF DESCRIPTION OF THE INVENTION

This invention relates to a method for the production of high octane gasolines or blends of octane improvers. More specifically, the invention is concerned with a process for obtaining highly branched oligomers of relatively low molecular weight normal olefinic compounds, the method or process being effected in the presence of certain acidic catalyst composites.

It is therefore an object of this invention to provide a process for the oligomerization of olefinic compounds.

A further object of this invetion is found in a process for obtaining highly branched chain oligomers of normal olefinic hydrocarbons.

In one aspect, an embodiment of this invention resides in a process for the preparation of a highly branched chain oligomer of an olefin-containing feedstock which comprises treating said feedstock at treating conditions in the presence of a catalyst comprising a fluorided aluminum phosphate, and recovering the resultant highly branched chain product.

A specific embodiment of this invention is found in a process for the preparation of a highly branched chain oligomer of an olefin-containing feedstock which comrises treating a feedstock comprising n-butene at a temperature in the range of from about 50° to about 350° C. and a pressure in the range of from about 100 to about 2500 pounds per square inch gauge (psig) in the presence of a catalyst comprising a fluorided aluminum phsophate which has been prepared by impregnating the aluminum phosphate with ammonium bifluoride, and recovering the resultant highly branched chain product.

Other objects and embodiments will be found in the following detailed description of the present invention.

DETAILED DESCRIPTION OF THE INVENTION

As hereinbefore set forth, the present invention is concerned with a process for producing oligomers of olefinic hydrocarbons to produce highly branched chain compounds, said compounds being useful as blending agents to improve the octane number of gasoline. The term "polymerization" as defined in the usual sense of the term will refer to molecules which possess a relatively high molecular weight as well as a relatively high number of individual units of the starting compound. In contrast to this, the term "oligomer" as used in the present specification and appended claims will refer to products which comprise the dimer, trimer, or tetramer of the starting compound. The oligomers and preferably the trimers, of the starting materials will possess a structure in which the chain of the molecule is highly branched, this particular configuration enhancing the octane number of the compound, thus making the product particularly desirable as an additive, or in some instances, as a high octane gasoline fuel per se.

The highly branched products are obtained by oligomerizing an olefin containing feedstock in which the olefins which are present in said feedstock will contain from about 3 to about 6 carbon atoms, and preferably from 3 to 4 carbon atoms. In addition, a particularly preferred characteristic of the olefins is that they are preferably normal in configuration, some specific examples of these olefins being propylene, 1-butene, 2-butene, 1-pentene, 2-pentene, 1-hexene, 2-hexene, 3-hexene, etc. In addition, the charge stock which is utilized to obtain the desired compounds of the present invention will also include some paraffinic counterparts of the olefins, the preferred olefin to paraffin ratio being from about 1 mole of olefins per 5 moles of paraffin to 5 mols of olefin per mole of paraffin or higher.

The oligomerization of the aforementioned olefins to obtain a highly branched chain product is effected at treatment conditions which may include a temperature in the range of from about 50° up to about 350° C. or more and superatmospheric pressures ranging from about 100 to about 2500 psig. It is contemplated that the pressures which are used may be afforded by the autogeneous pressure of the olefin which is undergoing oligomerization when the olefin is in gaseous form and by the addition of a substantially inert gas such as nitrogen, helium, argon, etc. when the olefin charge stock is in liquid form. Alternatively, if so desired, the gaseous olefin in the charge stock may afford only a partial pressure of the desired operating pressure, the remainder then also being afforded by the presence of an inert gas such as those hereinbefore set forth. In addition to these operating conditions, it is also contemplated within the scope of this invention that, if so desired, an isoolefin may be blended in the charge stock, said isoolefin when present being in a range of from about 1 to about 10% or higher by weight of the total charge stock.

The oligomerization of the olefin is effected in the presence of an acidic catalyst, the preferred catalyst being a fluorided aluminum phosphate. The catalyst which is utilized in the present invention may be prepared by forming an alumina sol in which aluminum is digested in hydrochloric acid. Following the digestion of the aluminum in the acid, phosphoric acid is blended into the sol preferably in a ratio of one mole of phosphoric acid per mole of aluminum, the blending being effected at ambient temperature and pressure. After blending of the phosphoric acid and the sol has been completed, the resulting mixture is neutralized in order that the desired gelation may be effected within a reasonable time and which will form spheres which possess desirable physical characteristics such as rigidity, etc. The neutralization is effected by the addition of an amine compound such as urea, hexamethylenetetramine which is formed by the reaction of formaldehyde with ammonia, aryl amines, mixtures of ammonium acetate and ammonium hydroxide, etc. The neutralized mixture is then chilled to a temperature which is subambient in nature, that is, to a temperature in the range of from about 5° to about 10° C.

The sol is then passed into a suspending medium which is immiscible with water, the suspending medium being maintained at an elevated temperature in order to obtain gelation within a desired time. The temperature of the suspending medium is usually in the range of from about 80° to about 105° C., and preferably within a range of from about 95° to about 99° C. Temperatures which are below the range hereinbefore indicated require setting times which are too long, while on the other hand, temperatures greater than those in the range result in vaporization of the water with a concomitant cracking of the resulting spheres. Any suitable water immiscible suspending liquid may be employed, particularly suitable suspending liquids comprising a refined mineral oil or other similar materials which will allow the droplets to settle at a rate such that the aluminum phosphate will set into a firm hydrogel during the passage of the drop through the fluid medium. After formation of the spheres they are then aged in the forming oil in a closed vessel at 110° C. to 160° C. and 50 to 150 psig for 1 to 5 hours.

Upon completion of the aging period, the spheres are washed with water containing NH$_4$OH at about 95° C. to remove any impurities or other materials which may still be present, the washing of the spheres being effected in any suitable manner such as percolation utilizing either an upward or downward flow of water. Following the washing, the spheres are then dried and calcined at a temperature ranging from about 500° to about 700° C. for a period in the range of from about 2 to about 12 hours or more in duration.

The catalyst composite which is utilized to obtain a highly branched chain oligomer is then prepared by impregnating the spheres with a fluorine-containing compound in either a gaseous, aqueous, or nonaqueous medium. The impregnation is effected when using a liquid medium by placing the spheres in an aqueous solution or water-soluble fluoride-containing compounds such as aluminum fluoride, ammonium fluoride, ammonium bifluoride, antimony fluoride, nickel fluoride, boron fluoride, hydrofluoric acid, etc., or a nonaqueous solution of titanium fluoride, etc. at room temperature and atmospheric pressure. The amount of fluorine in the fluoride-containing compound will be sufficient to impart a fluoride content to the finished catalyst in the range of from about 1% to about 10% by weight of the catalyst composite. If so desired, separate impregnations of the aluminum phosphate support with metal nitrates or acetates and a fluoride component may be carried out to prepare the desired catalyst system.

Alternatively, if so desired, the aluminum phosphate spheres may be impregnated by subjecting the spheres to contact with gaseous boron trifluoride for a time sufficient to again impart a fluoride content to the catalyst within the range hereinbefore set forth. After contact time has terminated, the fluorided aluminum phosphate catalyst is recovered, dried and recalcined again at a temperature in the range of from about 300° to about 600° C. to afford the finished catalyst composite.

The process of the present invention involving the preparation of highly branched chain oligomers of olefin-containing feedstocks may be accomplished in any manner and may comprise either a batch or continuous type operation. When a batch type operation is employed, a quantity of the fluorided aluminum phosphate catalyst is placed in an appropriate reaction apparatus such as an autoclave of the rotating or mixing type. The feedstock in either gaseous or liquid form admixed with, if so desired, paraffins and/or isoolefins may be charged to the reactor which has been sealed. The reactor is then heated to the desired operating temperature within the range hereinbefore set forth and pressured to the desired operating pressure. After allowing the reaction to proceed for a predetermined period of time, which may range from about 0.5 up to about 10 hours or more in duration, heating is discontinued. After the autoclave and contents thereof have returned to room temperature, the excess pressure, if any, is discharged and the autoclave is opened. The reaction mixture is recovered, separated from the catalyst, and subjected to separation operations such as fractional distillation whereby the desired highly branched chain oligomers may be separated and recovered.

It is also contemplated within the scope of this invention that the oligomerization reactions may be effected in a continuous manner of operation. When this type of operation is employed, the quantity of the catalyst comprising the fluorided aluminum phosphate is placed in an appropriate zone which is maintained at the proper operating conditions of temperature and pressure. The feedstock is continuously charged to the zone and after passsage through the zone in contact with the catalyst for a predetermined period of time, the reactor effluent is continuously withdrawn and separated by conventional means whereby any unreacted starting materials will be recycled to the reaction zone while the desired oligomers are recovered.

Due to the nature of the catalyst, it is possible to effect the continuous manner of operation in a variety of ways. For example, the oligomerization of the olefins may be effected while using a fixed bed type of operation in which the catalyst is positioned as a fixed bed in the reaction zone and the feedstock is passed over the catalyst in either an upward or downward flow. Likewise, if so desired, a moving bed type of operation may be employed in which the catalyst and the feedstock are passed through the reaction zone while moving the catalyst bed through said zone either concurrently or countercurrently to each other. A third type of operation which may be employed comprises the slurry type of operation in which the catalyst is carried into the reaction zone as a slurry in the feedstock. Whichever of the aforementioned methods are employed, the reactor effluent is continuously withdrawn and treated in a manner similar to that hereinbefore set forth.

The following examples are given for purposes of illustrating the process of the present invention and to emphasize the advantage which is enjoyed by the present catalyst system over previous catalyst systems with regard to the obtention of more highly branched chain oligomers. However, it is to be understood that these examples are merely illustrative in nature and that the present process is not necessarily limited thereto.

EXAMPLE I

A catalyst was prepared by charging alumina spheres to a one-liter autoclave which was then sealed and boron trifluoride added thereto. The autoclave was heated to a temperature of 300° C. and maintained thereat for a period of three hours. At the end of this time, heating was discontinued and after the autoclave had returned to room temperature, the fluorided alumina catalyst was unloaded. The catalyst spheres were then heated in a tubular furnace in a flow of air at a temperature of 350° C. for a period of three hours.

The oligomerization of olefins using this catalyst was effected by placing 50 cc of the fluorided alumina which contained 1.2% by weight of boron and 7.0% by weight of fluorine in a stainless steel tube which had a ⅞" inner diameter. The tube was heated to an inlet temperature of 135° C. and a charge stock comprising a mixture of 60% by weight of butene-2 and 40% by weight of n-butane was charged to the tube at a liquid hourly space velocity of 0.98 (based on the butene-2) while maintaining a pressure of 1000 psig. The effluent which was recovered from the reactor was analyzed, the results being that there had been a 65.2% conversion of the butene-2, the distribution of the $C_8$ dimer being hereinafter set forth.

EXAMPLE II

In a manner similar to that set forth in Example I above, a catalyst was prepared by charging 82 grams (190 cc) of aluminum phosphate spheres which had been obtained from a 1:1 mole ratio of alumina to phosphoric acid to a one-liter autoclave. The autoclave was sealed and 10 grams of boron trifluoride was charged thereto. Following this the autoclave was heated to a temperature of 300° C. and maintained thereat for a period of three hours. At the end of this time, heating was discontinued and after the autoclave had returned to room temperature, the fluorided aluminum phosphate was unloaded and placed in a tubular furnace. The furnace was heated to a temperature of 350° C. and maintained thereat for a period of three hours while calcining the spheres in an air atmosphere. At the end of the three hour period, heating was discontinued and the catalyst, which contained 0.2% by weight of boron and 2.6% by weight of fluorine, was recovered.

The catalyst prepared according to the above paragraph in an amount of 50 cc was placed in a reactor comprising a stainless steel tube having a ⅞" inner diameter. The tube was heated to an inlet temperature of 138° C. and a charge stock comprising a mixture of 60% by weight of butene-2 and 40% by weight of n-butane was charged to the reactor at a liquid hourly space velocity of 0.98 (based on the butene-2 charge) while maintaining a pressure of 1000 psig. The effluent from the reactor was analyzed, said analysis showing a 65.1% conversion of the butene-2. The make-up of the dimers is set forth in Table 1 below in which a comparison is set forth between the dimers obtained in this experiment with the dimers obtained in the experiment set forth in Example I above. Catalyst "A" is the catalyst prepared according to Example I above, that is, a fluorided alumina, while catalyst "B" is the catalyst prepared according to Example II, that is, a fluorided aluminum phosphate.

TABLE 1

| % $C_8$ Isomers | Catalyst A | Catalyst B |
| --- | --- | --- |
| Methylheptene | 2.9 | 1.4 |
| Dimethylhexene | 96.8 | 94.7 |
| Trimethylpentene | 0.3 | 3.9 |

As is evident from a comparison of the dimers obtained by the oligomerization of a butene-2 charge stock, the catalyst of the present invention, that is, a fluorided aluminum phosphate, will permit the recovery of a dimer product which contains a more highly branched product, namely trimethylpentenes, in an order of magnitude greater than that which is obtained when using a catalyst comprising only a fluorided alumina. A fraction of the product which had a boiling point within the range of from 204° to 393° F. was tested and found to have a research octane number of 96.7.

EXAMPLE III

In this example a catalyst may be prepared by impregnating aluminum phosphate with a solution of ammonium bifluoride for a time sufficient to impart about 2.5% by weight of fluorine to the aluminum phosphate. The impregnated aluminum phosphate may then be washed with water, dried and the fluorided aluminum phosphate calcined at a temperature of about 350° C. for a period of about 3 hours. The catalyst which may be prepared according to this method may then be placed in a stainless steel reactor and a charge stock comprising a mixture of pentene-2 and n-pentane may be charged to the reactor at a liquid hourly space velocity of about 1 while maintaining a pressure of 1000 psig and an operating temperature of about 150° C. After passage through the catalyst bed, the effluent may be recovered and the product comprising a mixture of methyl nonene, dimethyl octene and trimethyl heptene may be recovered therefrom.

It is also contemplated that other fluorided aluminum phosphate catalysts may be prepared by impregnating aluminum phosphate spheres which may be obtained from a 1:1 mole ratio of alumina to phosphoric acid with an aqueous solution of hydrofluoric acid, an aqueous solution of antimony fluoride or nonaqueous solution of titanium fluoride followed by drying and calcination. The fluorided aluminum phosphate catalyst which may contain about 2.5% by weight of fluorine may then be used to oligomerize a mixture of propylene and propane or a mixture of hexene-2 and n-hexane at reaction conditions similar to those hereinbefore set forth to obtain highly branched dimers of the olefinic feedstock. In addition, if so desired, about 5% by weight of isohexene may be added to the charge stock of hexene-2 and n-hexane to increase the branching of the dimer.

We claim as our invention:

1. A process for the preparation of a highly branched chain oligomer of an olefin-containing feedstock which comprises contacting said feedstock at a temperature in the range of from about 50° to about 350° C. and a pressure in the range of from about 100 to about 2500 pounds per square inch gauge with a catalyst comprising a fluorided aluminum phosphate, and recoving the resultant highly branched chain product.

2. The process as set forth in claim 1 in which the olefins in said olefin-containing feedstock possess from about 3 to about 6 carbon atoms.

3. The process as set forth in claim 1 in which said olefins are normal olefins.

4. The process as set forth in claim 1 in which said highly branched chain product is a dimer of said olefins in said olefin-containing feedstock.

5. The process as set forth in claim 1 further characterized in that from about 1% to 10% by weight of an isoolefin is blended into said feedstock.

6. The process as set forth in claim 1 in which said catalyst is prepared by impregnating an aluminum phosphate with a fluorine-containing compound, drying and recovering the resultant catalyst.

7. The process as set forth in claim 6 in which said impregnation is effected in a gaseous, aqueous or nonaqueous medium.

8. The process as set forth in claim 6 in which said fluoring-containing compound is ammonium bifluoride.

9. The process as set forth in claim 6 in which said fluorine-containing compound is boron trifluoride.

10. The process as set forth in claim 6 in which said fluorine-containing compound is hydrofluoric acid.

11. The process as set forth in claim 6 in which said fluorine-containing compound is antimony fluoride.

12. The process as set forth in claim 6 in which said fluorine-containing compound is titanium fluoride.

* * * * *